United States Patent [19]

Brader

[11] 4,050,158
[45] Sept. 27, 1977

[54] ARCH FORM COMPONENT

[76] Inventor: Allen C. Brader, 1350 Hamilton St., Allentown, Pa. 18102

[21] Appl. No.: 688,786

[22] Filed: May 21, 1976

[51] Int. Cl.² ............................................. A61C 7/00
[52] U.S. Cl. ................................................... 32/14 A
[58] Field of Search ....................................... 32/14 A

[56] References Cited

U.S. PATENT DOCUMENTS 1,481,861   1/1924   Eaton .................................. 32/14 A

OTHER PUBLICATIONS

Brader, Dental Arch Related with Intraoral Forces, American Journal of Orthodontics U61, No. 6, p. 541, June 1972.

*Primary Examiner*—Robert Peshock
*Attorney, Agent, or Firm*—Lockwood, Dewey, Zickert & Alex

[57] ABSTRACT

Orthodontic arch form of wire, or other resilient materials, and method of making same, having a compound elliptical shape wherein the form is generated by plotting three foci falling at the apices of an isoceles triangle and utilizing a string or the like in a closed loop of a length greater than the sum of the sides of the triangle to be restrained at the foci during the recording of the form by movement of a recording instrument restrained by the string.

13 Claims, 4 Drawing Figures

ARCH FORM COMPONENT

This invention relates in general to an orthodontic appliance, and more particularly to a preformed arch form of resilient wire or other suitable material to be used in an orthodontic system together with a method of making the arch wire.

Orthodontic systems for providing orthodontic treatment to patients essentially utilize brackets and/or tubes anchored to the teeth and arch forms or wires connected to the brackets and the tubes for storing energy and releasing forces over protracted intervals to obtain tooth movement in controlled directions for accomplishing the objectives of orthodontic treatment. The present invention concerns an arch form and a method for making same which is unique and which will better achieve the desired orthodontic treatment objectives.

There are three fundamental characteristics of human dental arch biology or growth recognized by orthodontists and which include (1) variations in arch size, (2) differences in arch form, and (3) translation in space. The present invention accurately reflects these characteristics as well as those due to growth, so that the physiological equilibrium of a patient's teeth is little disturbed during treatment and the best possible results can be achieved, thereby reducing post-treatment changes and consequently attaining long-term stability of the corrected dentition. Further, the optimum arch curve, as established in the present invention, assists the orthodontist in developing the best possible orthodontic treatment plan for a patient. The present invention further provides correlated maxillary and mandibular arch forms.

Heretofore, it has been known to provide arch forms of various configurations. The most common has been in the form of a U shape where the anterior part adapted to fit along the anterior teeth has been in the form of an arc of a circle, while the posterior projecting portions have extended merely in the form of straight lines. It has further been known to provide parabolically formed and elliptically formed arch wires as shown in U.S. Pat. No. 3,593,421. However, these previous forms have provided only rough approximations to the optimum arch form compatible with the physiological equilibrium of the teeth of a patient. Inaccurate arch forms employed in treatments predispose post-treatment dental instability. Further, it has not previously been known to distinguish between maxillary and mandibular arch forms which are nonetheless correlated to each other for specific individual orthodontic cases.

It is therefore an object of the present invention to provide a new and improved preformed arch form for use in an orthodontic system and a method of making such an arch wire.

A further object of this invention lies in the provision of a new and improved arch wire shape which, in geometry, is of compound elliptical form, and a method of making same.

A still further object of this invention is in the provision of a compound elliptically formed arch wire capable of defining an optimum arch form compatible with the physiological equilibrium of a pateint's teeth.

It is a still futher object of the present invention to provide correlated maxillary and mandibular preformed arch wires having a compound elliptical form.

Other objects, features and advantages of the invention will be apparent from the following detailed disclosure, taken in conjunction with the accompanying sheet of drawings, wherein like reference numerals refer to like parts, in which.

Figure 1:
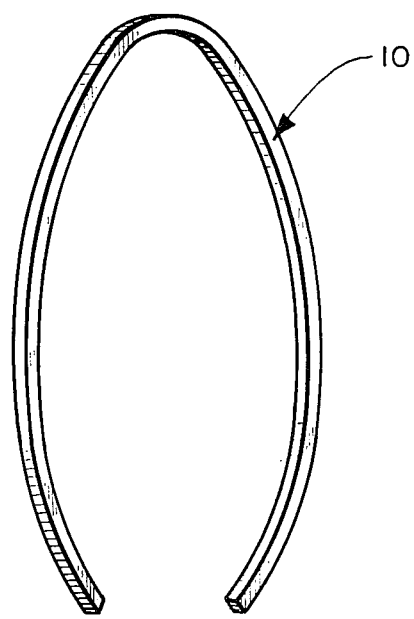
FIG. 1 is a perspective view of a preformed arch wire according to the present invention.
Figure 2:
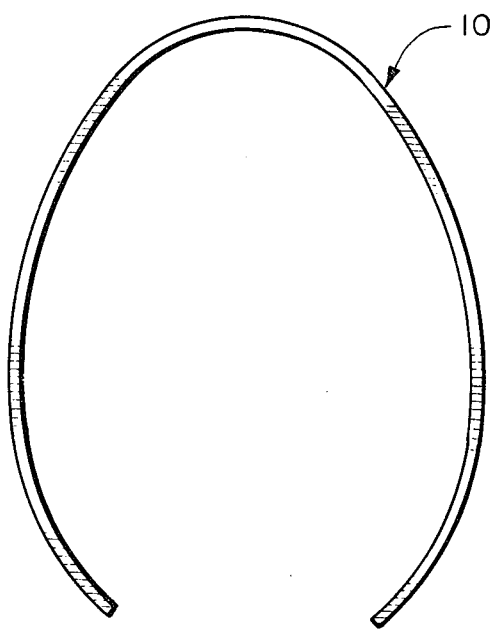
FIG. 2 is a top plan view of a preformed arch wire according to the present invention.

A preformed arch wire according to the present invention is shown in FIGS. 1 and 2 and generally indicated by the numeral 10. While this arch wire is shown to have a square in cross section configuration for use particularly in connection with the well known edgewise technique or orthodontic system, it should be appreciated that the arch wire may be circular in cross section for use with either the edgewise technique or the well known Begg light-wire technique. Further, the arch form of the present invention could be used with any othe multiband and bracket orthodontic system as it should be appreciated that the arch form is intended to consider the three fundamental characteristics of human dental arch growth so that the teeth of a patient will ultimately be positioned along an optimum curve or dental arch compatible with the physiological equilibrium of the teeth of that patient. It should be appreciated that prior to orthodontic treatment the teeth of a patient exist in a state of equilibrium. Accordingly, it is the goal of the orthodontist to carry out orthodontic treatment so that the teeth of the patient will ultimately be positioned along a curve representing natural dental equilibrium positions in order to provide the best possible results which would best prevent post-treatment recurrence of dental malocclusion, thereby insuring the best post-treatment dental stability.

It can be further appreciated that the present invention relates to an arch form that considers the growth characteristics of human dental arches in change in size, change in form and translation in space. The compound elliptical arch form of the present invention further assists the orthodontist in developing a proper treatment plan for predetermination of the optimum curvature of the corrected arch prior to treatment.

Figure 3:
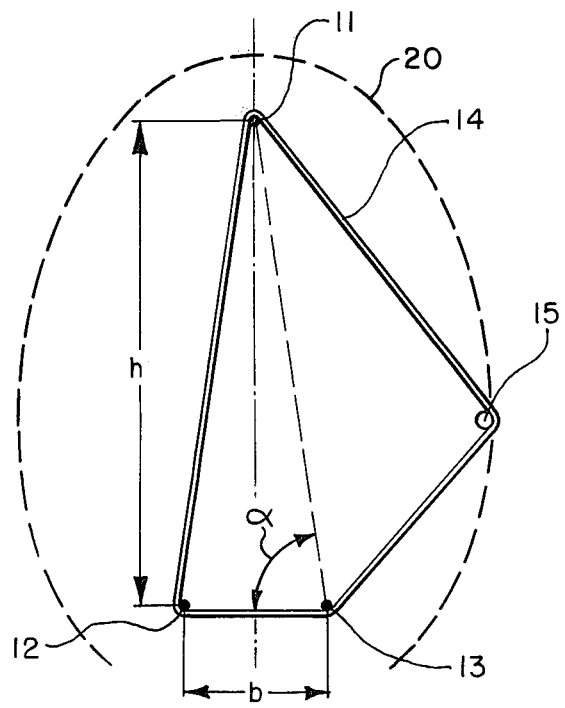
FIG. 3 is a layout for illustrating the manner in which the arch form of the present invention is generated.

A preformed arch wire of the present invention is constructed on the template of an arch form drawn or otherwise recorded on paper in a fashion as illustrated in FIG. 3. While heretofore known elliptical forms have been made by use of a conventional pair of foci and the use of a string loop for generating a simple elliptical form in a well known manner, the compound elliptical form of the present invention is made by use of three foci together with a loop of string. As seen in FIG. 3, foci 11, 12 and 13 are plotted such that they fall at the apices of an isoceles triangle. The height of the triangle is designated as $h$, the base is designated as $b$ and the base angles are designated as $a$.

Figure 4:
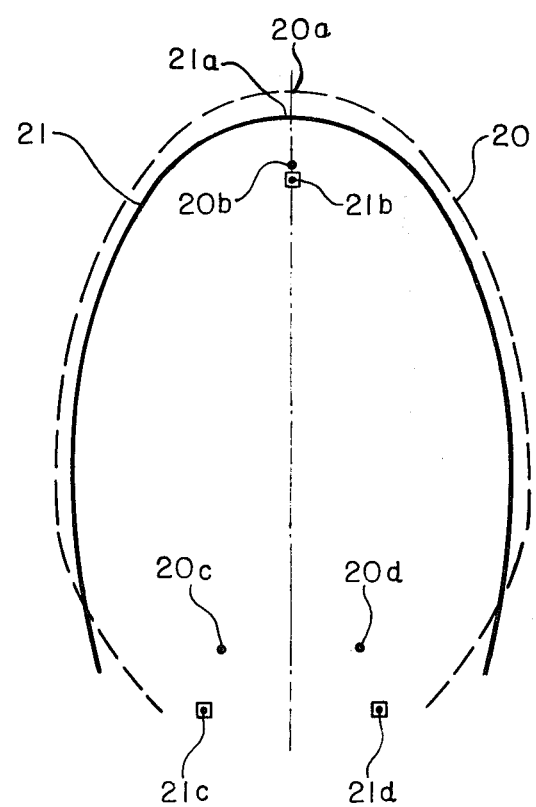
FIG. 4 is a layout illustrating the plan of geometry for constructing the correlated maxillary and mandibular arch forms according to the present invention.

Following the plotting of the foci which is accomplished by making the height three to four times the base and the base angles on the order of 79° to 85°, and preferably 81° to 83.5°, a loop of string 14, sized greater than the sum of the sides of the isoceles triangle and such that it will define the desired maximum arch width of a particular form, is used to generate the compound elliptical form by use of a suitable recording instrument 15. It will be appreciated that the arch width of a particular form is measured at the buccal sides of the widest erupted teeth along the dental arch of a patient. This will normally be in the molar region of the dental arch. The point along the dash curve shown in FIG. 3 where the instrument 15 is shown generally represents the maximum arch width of this curve. This point, in relation to the isoceles triangle, will be located more than half way toward the base from the top point 11. By restricting the position of the string 14 according to the foci 11, 12 and 13, movement of the recording instrument 15 about the foci as constrained by the string will establish the compound elliptical arch form according to the invention as indicated by the dash curve representing an arch form 20, as seen in FIG. 4.

Correlated maxillary and mandibular arch forms can be made according to the present invention. It should be appreciated that the mandibular arch form is contained within and is sized to reside two to four millimeters inside the maxillary arch form. This is particularly evident at the midline of the arch form and is determined there at the front ends of the curves. Similarly, the corresponding points at the maximum arch width would be spaced two to four millimeters apart. However, the mandibular arch form curves as seen in FIG. 4 are more elongated or oblate than the maxillary arch form curves. As seen in FIG. 4, the midline point of the maxillary arch form is at 20a, while the midline point of the mandibular arch form 21 is at 21a. Normally for correlated arch forms these points would be 2 to 4 millimeters apart. The foci for generating the mandibular arch form therefore are positioned accordingly to accomplish the generation of the mandibular arch form in correlated relation to the maxillary arch form. As seen in FIG. 4, the foci for the maxillary arch form 20 are designated 20b, 20c and 20d, while the foci for the mandibular arch form 21 are designated 21b, 21c and 21d. It can be appreciated that the length of the loop of string for generating the mandibular arch form would be adjusted to bring the midline point 21a inside the midline point 20a of the maxillary arch form and to bring the maximum arch width points of the mandibular arch form within those of the maxillary arch form. Further, the foci are plotted to develop a more elongated triangle.

It has been found that arch forms having arch widths of between 48 and 68 millimeters can be generated by the measurements indicated in the following table relative the positions of the foci and the string length.

triangle. It will be further noted that the range of the base angles is from 81° to 83.5° in connection with the maxillary and mandibular arch curves.

Accordingly, an arch wire formed according to the present invention in the form of a compound ellipse may be formed with the data set out in the above table. However, it can be appreciated that this data may vary slightly within the scope of the invention.

It will be understood that modifications and variations may be effected without departing from the scope of the novel concepts of the present invention, but it is understood that this application is to be limited only by the scope of the appended claims.

The invention is hereby claimed as follows:

1. A method of making a compound elliptical arch form for use in an orthodontic system comprising the steps of, plotting three foci so that connections therebetween would generate an isoceles triangle, preparing a closed loop of string of a length greater than the sum of the sides of the triangle and such as to produce a given arch width, generating and recording an arch form by using the string and the foci, and bending a resilient wire according to the arch form.

2. The method as defined in claim 1, wherein the step of plotting the foci includes dimensioning the triangle so that the base angles of said triangle are on the order of 79° to 85°.

3. The method as defined in claim 1, wherein the step of plotting the foci includes dimensioning the triangle so that the height of said triangle is at least equal to the arch width.

4. The method as defined in claim 1, wherein the step of plotting the foci includes dimensioning the triangle so that the height of the triangle is on the order of three to four times the length of the base.

5. The method as defined in claim 1, wherein the step of plotting the foci includes dimensioning the triangle so that the height of the triangle is on the order of three to four times the length of the base, and the base angles of said triangle are on the order of 79° to 85°.

6. An arch form produced by the method defined in claim 1.

7. A method of making correlated maxillary and mandibular preformed arch wires for use in orthodontic system comprising the steps of making the maxillary arch wire in accordance with a compound elliptical form, and making the mandibular arch wire in accordance with a compound elliptical form such that when

|  | Maxillary Arch | | | | Mandibular Arch | | | |
| --- | --- | --- | --- | --- | --- | --- | --- | --- |
| Arch Width | Height (h) | Base (b) | Base Angles (a) | String Length | Height (h) | Base (b) | Base Angles (a) | String Length |
| 48 mm | 48 mm | 14 mm | 82.5° | 126 mm | 53 mm | 18 mm | 82.0° | 140 mm |
| 52 mm | 55 mm | 16 mm | 82.5° | 136 mm | 60 mm | 20 mm | 81.5° | 152 mm |
| 56 mm | 63 mm | 17 mm | 83.5° | 158 mm | 68 mm | 22 mm | 83.0° | 170 mm |
| 60 mm | 67 mm | 18 mm | 82.5° | 170 mm | 73 mm | 23 mm | 81.0° | 182 mm |
| 64 mm | 77 mm | 19 mm | 84.0° | 188 mm | 85 mm | 24 mm | 82.5° | 210 mm |
| 68 mm | 82 mm | 20 mm | 83.5° | 206 mm | 92 mm | 26 mm | 83.0° | 224 mm |

From the table above, it can be appreciated that for the various arch widths the dimension of the height of the isoceles triangle is three to four times the dimension of the base for both the maxillary and mandibular arches. The length of the string is greater than the sum of the sides of the triangle. Further, the length of the loop of string is such that it will define the arch width desired when the curve is generated by use of a recording instrument such as a pencil or the like when the string is restrained about the three foci of the isoceles the arch wires are placed in substantially superposed relation the midline point of the mandibular arch wire is spaced slightly inside the midline point of the maxillary arch wire and the maximum arch width points of the mandibular arch wire is spaced inside the maximum arch width points of the maxillary arch wire.

8. The method of claim 7, wherein the midline and maximum arch width point spacing is about two to four millimeters.

9. An arch form produced by the method defined in claim 7.

10. A method of making correlated maxillary and mandibular preformed arch wires for use in an orthodontic system comprising the steps of making the maxillary arch wire in accordance with a compound elliptical form, plotting three foci so that connections therebetween would generate an isoceles triangle, preparing a closed loop of string of a length greater than the sum of the sides of the triangle and such as to produce a given arch width, generating and recording a maxillary arch form by using the string and the foci, and bending a resilient wire according to the arch form, and making the mandibular arch wire in accordance with a compound elliptical form including plotting three foci so that connections therebetween would generate an isoceles triangle, wherein the foci are plotted such that the height to base ratio of the triangle for the maxillary arch form is greater than the height to base ratio of the triangle for the mandibular arch form, preparing a closed loop of string of a length greater than the sum of the sides of the triangle and such as to produce a given arch width, generating and recording a mandibular arch form by using the string and the foci, and bending a resilient wire according to the mandibular arch form.

11. The method as set forth in claim 10, wherein the height of the triangles for both arches is on the order of three to four times the base.

12. The method as set forth in claim 7, wherein the base angles of said triangles are on the order of 79° to 85°.

13. An arch form produced by the method defined in claim 10.

* * * * *

UNITED STATES PATENT AND TRADEMARK OFFICE
CERTIFICATE OF CORRECTION

PATENT NO. : 4,050,158
DATED : September 27, 1977
INVENTOR(S) : Allen C. Brader

It is certified that error appears in the above—identified patent and that said Letters Patent are hereby corrected as shown below:

```
Col. 1, line 63, change "pateint's" to --patient's--;
Col. 2, line 23, change "othe" to --other--;
Col. 4, line 44, after "in" insert --an--;
Col. 6, line 12, change "7" to --11--;
OTHER PUBLICATIONS, line 1, after "Arch" insert --Form--; and
                   line 2, change "U61" to --Vol. 61--.
```

Signed and Sealed this

Seventeenth Day of October 1978

[SEAL]

Attest:

RUTH C. MASON
*Attesting Officer*

DONALD W. BANNER
*Commissioner of Patents and Trademarks*